United States Patent
Grootjans et al.

(10) Patent No.: US 6,368,811 B1
(45) Date of Patent: Apr. 9, 2002

(54) SYNDECAN INTERACTING PROTEINS AND THE USE THEREOF

(75) Inventors: Jan Grootjans, Leuven; Pascale Zimmermann, Opheylissem; Guido David, Leuven, all of (BE)

(73) Assignee: Vlaams Interuniversitair Instituut Voor Biotechnologie, Zwijnaarde (BE)

( * ) Notice: Subject to any disclaimer, the term of this patent is extended or adjusted under 35 U.S.C. 154(b) by 0 days.

(21) Appl. No.: 09/427,261

(22) Filed: Oct. 25, 1999

Related U.S. Application Data

(63) Continuation of application No. PCT/EP98/02464, filed on Apr. 22, 1998.

(30) Foreign Application Priority Data

Apr. 25, 1997 (EP) ............................................. 97201233

(51) Int. Cl.[7] .......................... G01N 33/53; C07K 14/00
(52) U.S. Cl. .......................... 435/7.1; 530/300; 530/350
(58) Field of Search ........................ 435/6, 69.1, 320.1, 435/7.1; 436/501; 536/24.1; 514/2, 44; 530/350, 300

(56) References Cited

U.S. PATENT DOCUMENTS 5,648,465 A * 7/1997 Margolis et al. ............ 530/350

OTHER PUBLICATIONS

Lin et al.; Characterization of a Novel Melanoma Differentiation–Associated Gene, mda–9, That is Down–Regulated During Terminal Cell Differentiation; Molecular and Cellular Differentiation; 1996; pp. 317–333; vol. 4 [4]; CRC Press, Inc.

Lin et al.; Melanoma Differentiation Associated Gene–9, Mda–9, Is a Human Gamma Interferon Responsive Gene; Gene; 1998; pp. 105–110; Elsevier Science B. V.

Grootjans et al.; Syntenin, a PDZ Protein That Binds Syndecan Cytoplasmic Domains; Cell Biology; Dec. 1997; pp. 13685–13688; vol. 94; Proc. Natl. Acad. Sci. USA.

Carey; N–Syndecan: Structure and Function of a Transmembrane Heparan Sulfate Proteoglycan; Perspectives on Developmental Neurobiology; 1996; pp. 331–346; vol. 03; Overseas Publishers Association; Malaysia.

Chien et al.; The Two–hybrid System: A Method to Identify and Clone Genes for Proteins that Interact with a Protein of Interest; Proc. Natl. Acad. Sci, USA; Nov. 1991: pp. 9578–9582; vol. 88.

EMBL Database entry HSU3463; Accession No. U83463; 3. Apr. 1997; Burbelo P.D.: 'A new family of scaffold proteins.' XP002084506; see abstract.

EMBL Database entry HS104343; Accession No. W37104; May 17, 1996; Hillier L. et al.; 'The WashU–Merck EST project.' XP002040759; see abstract.

EMBL Database entry HS661323; Accession No. W07661: Apr. 27, 1996; Hillier L. et al.; XP002040760; see abstract.

EMBL Database entry HSHBC4245; Accession No. D82376; Feb. 9, 1996; Takada J.; XP002040761; see abstract.

EMBL Database entry HS302G12B; Accession No. D57438; Aug. 27, 1995; Fujiware T. et al.; XP002040762; see abstract.

* cited by examiner

Primary Examiner—Karen Cochrane Carlson
(74) Attorney, Agent, or Firm—TraskBritt

(57) ABSTRACT

The invention relates to the identification of a new protein that binds to the cytoplasmic domain of syndecan. This new protein, denominated as "syntenin", contains 298 amino acids and is characterized by a tandem repeat of PDZ-domains that reacts with the C-terminal amino acid sequence of syndecans. The amino-terminal region of syntenin further comprises five tyrosine residues whereas no tyrosine residues are present in the remaining part of the protein. The present invention further discloses a nucleic acid encoding syntenin, a method to screen for components interfering with the syndecan-syntenin interaction, a method for diagnosing Alzheimer's disease, inflammatory diseases, and malignancies and a pharmaceutical composition for healing the latter diseases.

9 Claims, 1 Drawing Sheet

Figure 1  eGFP
Figure 2  eGFP SYCL

SYNDECAN INTERACTING PROTEINS AND THE USE THEREOF

RELATED PRIOR FOREIGN/PCT APPLICATIONS

This application is a continuation of International Application PCT/EP98/02464 filed Apr. 22, 1998, which claims priority from European application 97201233 filed on Apr. 25, 1997.

TECHNICAL FIELD

The present invention relates to syndecan interacting protein(s) and the use thereof.

BACKGROUND

The invention relates to the identification of a protein that binds to the cytoplasmic domain of the syndecan. This protein, now called syntenin, contains a tandem repeat of PDZ-domains that reacts with the FYA C-terminal amino acid sequence of the syndecans (Trends Biochem.Sci., 20, p. 350, 1995: Origin of PDZ {DHR, GLGF}, by M. B. Kennedy). Endogenous syntenin appears to be localized to the cytoskeleton.

DISCLOSURE OF THE INVENTION

GFP-syntenin fusion-proteins decorate the plasma membrane and intracellular vesicles, where they co-localize and -segregate with syndecan cytoplasmic domains. Syntenin, therefore, is an unexpected candidate for connecting the cytoskeleton to heparan sulfate-assisted signal transduction pathways.

The syndecan cytoplasmatic link (sycl) protein or syndecan interacting protein is referred to by the name "syntenin", meaning "putting tension on the syndecans."

Heparan sulfate proteoglycans (HSPG) are proteins which are mostly associated with the cell membrane. The most characterizing feature of these proteins is that they are substituted with different heparan sulfate sugar derivatives which strongly determine the function of said protein. Basically there are two classes of membrane heparan sulfate proteoglycans. First the best characterized membrane proteoglycans are the syndecans, which have a membrane spanning core protein. The second class is the glypican family which are located at the cell surface and anchored in the cell membrane through GPI (glycosyl phosphatidyl inositol).

The existence of two distinct highly conserved multigene families of cell surface proteoglycans, the syndecan and glypican families respectively, suggests two distinctive cellular and/or subcellular pathways wherein these proteins will function. Ramifications within these pathways that are specified by the variations on a basic structural theme are realized by the various members of these families. The aforementioned HSPGs are involved in several physiological processes and play a definite role in the transmission of signals from outside a cell into the cell itself. Their their activities are characterized by the specific binding of heparan sulfate molecules to proteinase inhibitors, cell adhesion molecules or growth factors.

If the structure of HSPG is disturbed, abnormal cell growth and abnormal morphogenesis occur. Therefore it is of utmost importance to know and understand the structure-function relation of the proteoglycans and the way they transmit outside signals through the cell membrane into the cell, the so-called signal transduction cascade.

As mentioned above syndecans are transmembrane proteoglycans that place structurally heterogeneous heparan sulfate chains at the cell surface and a highly conserved polypeptide in the cytoplasm. Their versatile heparan sulfate moieties support various processes of molecular recognition, signaling and trafficking.

The cell surface heparan sulfate proteoglycans are at the cross-section of several different pathways. Their heparan sulfate moieties bind various differentiation-, growth-, and scatter factors, facilitate the occupation and activation of the corresponding signal-transducing receptors, and are involved in the internalization and clearance of the signaling complexes from the cell surface. They also assist receptors that are involved in cell—cell and cell-matrix adhesion, and assist scavenging receptors that are involved in the endocytosis and transcytosis of lipoproteins and lipases. They also bind and activate serine proteinase inhibitors and accelerate the reactions of these inhibitors with their targets. Proteolysis, lipolysis, mesoderm-induction, gastrulation, angiogenesis, neuritogenesis all appear to be regulated by or to depend on heparan sulfate, because this glycosaminoglycan is needed for the allosteric activation, approximation and compartmentalization of the reactants that are engaged in these processes.

In most cells syndecans represent the major source of cell surface heparan sulfate. The four known syndecans are small type I membrane proteins, with similar and simple domain organizations: a single ectodomain, membrane-span, and cytoplasmic domain. Except for the presence of three or four consensus sites for heparan sulfate attachment, near the amino-termini of the proteins, and a dibasic, presumably protease-sensitive site at the junctions with the membrane spanning segments, the ectodomains of the different syndecans have little in common. The structures of these ectodomains have also not been evolutionary conserved, except for these shared structural elements. The membrane-spanning and the small cytoplasmic domains of the syndecans, in contrast, show extensive structural similarity (60% sequence identity) and have been highly conserved during evolution. All four vertebrate syndecans and the single Drosophila syndecan share the amino acid sequence RM(K/R)KKDEGSY—depicted in one-letter code— in the membrane-proximal segments of their cytoplasmic domains, and the amino acid sequence EFYA—depicted in one letter code— at their C-termini. This suggests that the extracellular heparan sulfate moieties, the cytoplasmic protein moieties, and the contiguity of these moieties are essential for syndecan function. The syndecans may provide for a transmembrane link between extracellular heparin-steered processes and intracellular structural or regulatory proteins, and mediate outside-in or inside-out effects on signaling or effector systems.

BEST MODE OF THE INVENTION

In order to understand above mechanism/cascade a search for Syndecan cytoplasmic links (sycls) was initiated using the cytoplasmic domains of four different syndecans as baits in a yeast two-hybrid screening assay. The insert of one apparent truly positive clone (yielding HIS+ and LacZ+ phenotypes in combination with all four syndecan/Gal4 DNA-binding domain fusion constructs, but not with Gal4 DNA-binding domain alone or with p53 fused to the Gal4 DNA-binding domain) was sequenced, and used as a starting point to obtain a cDNA coding for the corresponding full length sycl protein.

The present invention concerns syndecan interacting protein(s) obtainable by a two-hybrid screening assay whereby as bait a cytoplasmic domain comprising the amino acid sequence FYA as C-terminal sequence as occurring in syndecan and as prey a cDNA library is used. For the purpose of the invention the cDNA library can be any suitable cDNA library, but preferably be a mammal, more preferably a human and most preferably a human liver cDNA library. The fall length sycl thus obtained consists of 298 aminoacids, and can be divided in three or four parts. The first amino-terminal region (aa 1–109) shows no striking homology to any known structural motif. It is relatively rich in proline and contains five tyrosines, while the remainder of the protein is free of tyrosine. Based on sequence alignments, the second (aa 101–193) and third (aa 194–274) regions of sycl appear to correspond to a tandem repeat of two PDZ domains. The sequence coding for the putative second PDZ domain is extended by 24 amino acids (aa 275–298), which may still be part of the second PDZ domain or compose a fourth separate C-terminal domain. PDZ domains have recently been recognized as one of the conserved modular structures that support protein—protein interactions and networking. PDZ domains mediate protein—protein interactions by binding to the carboxy-terminal ends of target proteins, and often occur in association with other functional modules, such as SH3 domains, protein tyrosine phosphatase domains, domains related to guanylate kinase (GUK), to band 4.1 protein, leucine zipper motifs, and additional PDZ domains. PDZ domains have now been discovered in a variety of proteins, and shown to bind to membrane channels, receptors (e.g. wingless and Notch), tumor supressor proteins (APC), GAPs and GEFs. These interactions appear to be involved in the formation of multimeric protein complexes that influence receptor positioning and clustering, and the connections of receptors and receptor-associated molecules to cytoskeletal proteins and downstream signal effectors. Further tests were aimed at investigating the involvement of the sycl PDZ domains in the syndecan-sycl interaction, and potential further links of sycl to the intracellular cytoskeleton.

The Genbank accession number for this sycl/syntenin cDNA and protein sequence according to the invention is AF000652.

The yeast two-hybrid system (Chien et al, 1991; P.N.A.S., 88, 9578–9582) was used to identify the domains of sycl and the residues in the syndecan cytoplasmic domains that are responsible for the syndecan-sycl interaction. Different parts of the original clone (3p11) and of the sycl cDNA were subcloned in the pGAD10 vector (Clontech Laboratories), to code for fusions between the activating domain of Gal4 (Gal4 AD) and various full length, truncated, deleted, point-mutated, or epitope-tagged versions of sycl. Full length sycl (tagged in the C-terminus with myc-epitope or not) and the original isolate (missing the first 91 aa of sycl) were able to interact with the full length syndecan (2 or 3) cytoplasmic domains, as revealed by growth on His- plates and b-gal activity. Even the fragment missing the first 112 amino acids of sycl is able to interact with the full length of syndecan. The N-terminal domain alone and either of the two PDZ domains alone were all inactive, suggesting that the paired PDZ domains are required for the binding interaction. Deletion of the complete N-terminal region (aa position 1–113), also abolished the interaction, indicating that the two PDZ domains and part of the N-terminal sequence are required (to allow the correct folding of the PDZ domains or for the interaction itself). It is not clear why the PDZ domains of sycl are not or less active separately. But a requirement for paired PDZ domains (for instance two PDZ1 or two PDZ2 domains) has also been observed for the interactions of the GRIP adaptor protein with AMPA receptors 12 and the interaction of hDlg with with the cytoplasmic domain of the Shaker-type K+channel.

The sycl binding sites in the syndecan cytoplasmic domain were deduced from the testing of a series of deletion- and alanine-substitution mutants of the syndecan-2 cytoplasmic domain. These mutants were cloned in pAS2, as Gal4 DNA-binding domain fusion proteins, and expressed as partners for the Gal4 activation domain-full length sycl fusion protein. All the C-terminal deletions and the substitutions of alanine for the F-residue at −2 and the Y-residue at −1, but not the alanine substitution for the E-residue at −3,abolished the binding interaction. Deletion of all but the last four residues from the cytoplasmic domain, only partially abolished the interaction (His-,but gal+). This localizes the binding site to the C-terminal FYA sequence of the syndecans, and appears consistent with the concept that PDZ proteins mediate protein—protein interactions by binding to the C-termini of proteins and discriminate among these sequences.

To examine the interaction between the syndecan cytoplasmic domain and sycl in systems other than yeast, the various sycl and syndecan constructs were also expressed as GST-fusion proteins (Glutathione S-Transferase), and used in ligand blot-assays and surface plasmon resonance experiments. In ligand blots, GST-sycl full length (FL) and GST-sycl M92 (sycl sequence starting at M92) fusion proteins failed to bind to GST itself, to itself or to fusion proteins composed of GST and to the C-terminal deletion, the F(C30)A or Y(C31)A mutants (at positions 30 and 31 respectively), of the syndecan-2 cytoplasmic domain. The same GST-sycl constructs, in contrast, bound to fusion proteins composed of GST and any of the other syndecan-2 mutants or four different wild type syndecan cytoplasmic domains. In biosensor experiments, a streptavidin-immobilized biotinylated synthetic peptide, representing the 32 cytoplasmic amino acids of syndecan-2, bound the GST-sycl FL and GST- sycl M92 proteins, but not fusion proteins composed of GST and parts of sycl containing only one of the two PDZ domains.

Unlike the yeast two-hybrid assay, the biosensor experiment showed some binding of sycl that missed all of the N-terminal domain but retained both PDZ domains. A calculation of the $k_{on}$ and $k_{off}$ values for the binding of sycl, from curves obtained at different concentrations of the GST-sycl FL or M92 fusion proteins and using the BIAcore2000 software, proved less relevant since the data were not consistent with a simple binding interaction, but the data suggest rapid dissociation ($k_{off}=10^{-3}$, if one would accept a A+B<=>AB interaction model). The sycl moiety itself, isolated from the fusion protein with the help of factor Xa, also bound to the synthetic peptide, indicates that the GST-moiety itself was not needed. No sycl-peptide binding interaction could be observed, however, when the GST-sycl proteins were immobilized on a biosensor chip coated with an anti-GST antibody and the peptide was perfused over the immobilized sycl. These data suggest that the sycl-syndecan interaction may be very transient and depend on cooperative syndecan interactions. This implies that sycl-syndecan interactions may require the clustering of the syndecans.

The subcellular expression of sycl and its potential colocalization with syndecan was investigated with the help of monoclonal antibodies raised against sycl fusion proteins. Association was investigated by immunohistochemistry, and through the overexpression of syndecans and Green Fluorescent Protein-fusion (GFP) proteins in CHO-cells. In non-transfectant CHO cells most of the sycl-immunoreactivity was associated with cytoplasmic fibrils, identifying sycl as a cytoskeleton-associated protein. These sycl-fibrils or sycl-decorated fibrils ran criss-cross through the cytoplasm, with a perinuclear rather than a subcortical distribution. Little or no membrane staining was observed in these cells, indicating sycl was scarce at this site or undetectable with the current tools. To investigate possible co-localisations and interactions of syndecans and sycl, CHO cells were stably transfected with an expression plasmid coding for human syndecan-1 (chosen because of the availability of a monoclonal antibody for the syndecan-1 cytoplasmic domain) or syndecan-2 were transiently supertransfected with plasmids coding for eGFP (enhanced green fluorescent protein) or an eGFP-sycl fusion-protein. CHO cells overexpressing eGFP-sycl showed a striking change in morphology in comparison to non-tranfected cells and cells expressing eGFP (see FIG. 1 and 2 respectively). These cells were larger and flatter, and were decorated with numerous membrane projections or filopodia. Often, these cells were also multinucleated. The eGFP-sycl protein autofluoresence was localized to the cytoplasm, to small intracellular vesicular structures, to the plasmamembrane, and partially colocalized with F-actin filaments, as revealed by staining with phalloidin-Texas Red-X. Green fluorescent eGFP-sycl transfectants were intensely stained by anti-sycl monoclonal antibody, indicating marked overexpression of sycl protein in these cells. Staining of the syndecan-1 double transfectants with antibody directed towards the cytoplasmic domain of syndecan-1 and Texas Red-X-labeled secondary antibody, showed partial colocalization of this syndecan domain and eGFP-sycl. No colocalization of green and red fluorescence was observed in control cells transfected with eGFP. Capping of the syndecan-1 cytoplasmic domain could be induced by mild and brief trypsinization of the cells at 4° C., followed by a 10–30 min reincubation of the cells at 37° C. Massive co-capping of the red (syndecan-1 cytoplasmic domain) and green fluorescence (GFP) was observed in eGFP-sycl expressing cells, but not in eGFP expressing cells, indicating colocalization of sycl and this syndecan domain during the capping process. Similar, but less perfect, colocalizations were observed with a syndecan-1 ectodomain antibody in the syndecan-1 transfectants, and with a syndecan-2 ectodomain antibody in the syndecan-2 transfectants. These data show that sycl associates with the cytoskeleton and with the cytoplasmic domains of the syndecans, and function as an adaptor molecule that links syndecan-supported recognition processes to intracellular signal-transduction, control, and -effector systems.

The current invention thus concerns an isolated nucleic acid sequence comprising the nucleotide sequence as provided in SEQ ID NO. 2 coding for a syndecan interacting protein or a functional fragment thereof. "Functional fragment" in this context means that said fragment to which subject it relates has substantially the same activity as the subject itself, although the form, length or structure may vary.

Furthermore a recombinant expression vector comprising said isolated nucleic acid sequence (in sense or anti-sense orientation) operably linked to a suitable control sequence belongs to the present invention and cells transfected or transduced with said recombinant expression vector also belong to the scope of the invention.

The current invention is not limited to the exact isolated nucleic acid sequence comprising the nucleotide sequence as mentioned in SEQ ID NO. 2 but also a nucleic acid sequence hybridizing to said nucleotide sequence as provided in SEQ ID NO. 2 or a functional part thereof. The present invention also encodes for a syndecan interacting protein or a functional fragment thereof.

As used herein, hybridization means is meant conventional hybridization conditions known to the skilled person, preferably appropriate stringent hybridization conditions. Hybridization techniques for determining the complementarity of nucleic acid sequences are known in the art. The stringency of hybridization is determined by a number of factors during hybridization, including temperature, ionic strength length of time and composition of the hybridization buffer. These factors are outlined in, for example, Maniatis et al. (1982) Molecular Cloning; A laboratory manual (Cold Spring Harbor Press, Cold Spring Harbor, N.Y.)

Another aspect of the invention is a polypeptide comprising the amino acid sequence according to SEQ.ID.NO. 1 or a functional fragment thereof. Specifically the polypeptide fragments with the amino acid sequence located between position 92 and 298 and more specifically between 113 and 298 in the current invention.

The scope of the present invention also includes variants or homologues of amino acids enclosed in the polypeptide wherein said amino acids are substituted by other amino acids obvious for a person skilled in the art without loosing their activity. The polypeptide or functional fragments of the present invention are not necessarily translated from the nucleic acid sequence according to the invention but may be generated in any manner, including for example, chemical synthesis, or expression of a recombinant expression system. A pharmaceutical composition comprising above mentioned nucleic acid(s) or a pharmaceutical composition comprising said polypeptide(s) also belong to the current invention. The nucleic acid and/or polypeptide according to the invention can be optionally used for appropriate gene therapy purposes. In addition a method for diagnosing, prognosis and/or follow-up of a disease by using the nucleic acid(s) according to the invention or by using the polypeptide(s) of the current invention.

A method of screening for components which affect the interaction between syndecan and syndecan interacting protein can be developed having the current knowledge of these syndecan interacting factors according to the invention. A diagnostic kit comprising the nucleic acid(s) and/or polypeptide(s) according to the invention for performing above mentioned method for diagnosing, prognosis and/or follow-up of a disease clearly belong to the invention as well. Some diseases in this respect are for instance Alzheimer disease or inflammatory diseases. Screening may also occur for cell malignancies and the activity of cytostatica thereupon.

A transgenic animal harbouring the nucleic acid(s) according to the invention in its genome also belong to the scope of this invention. With transgenic animal is meant a non-human animal which have incorporated a foreign gene (called transgene) into their genome; because this gene is present in germ line tissues, it is passed from parent to offspring establishing lines of transgenic animals from a first founder animal. It will be appreciated that when a nucleic acid construct is introduced into an animal to make it transgenic the nucleic acid may not necessarily remain in the form as introduced. By "offspring" is meant any product of the mating of the transgenic animal whether or not with another transgenic animal, provided that the offspring carries the transgene. In order to clarify what is meant in this description by some terms a further explanation is hereunder given.

The polypeptides of the present invention are not necessarily translated from a designated nucleic acid sequence;

the polypeptides may be generated in any manner, including for example, chemical synthesis, or expression of a recombinant expression system, or isolation from a suitable viral system. The polypeptides may include one or more analogs of amino acids, phosphorylated amino acids or unnatural amino acids. Methods of inserting analogs of amino acids into a sequence are known in the art. The polypeptides may also include one or more labels, which are known to those skilled in the art.

The terms "gene(s)," "polynucleotide," "nucleic acid sequence," "nucleotide sequence," "DNA sequence" or "nucleic acid molecule(s)" as used herein refers to a polymeric form of nucleotides of any length, either ribonucleotides or deoxyribonucleotides. This term refers only to the primary structure of the molecule. Thus, this term includes double- and single-stranded DNA, and RNA. It also includes known types of modifications, for example, methylation, "caps" substitution of one or more of the naturally occurring nucleotides with an analog.

An "expression vector" is a construct that can be used to transform a selected host cell and provides for expression of a coding sequence in the selected host.

A "coding sequence" is a nucleotide sequence which is transcribed into MRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances.

"Control sequence" refers to regulatory DNA sequences which are necessary to effect the expression of coding sequences to which they are ligated. The nature of such control sequences differs depending upon the host organism. In prokaryotes, control sequences generally include promoter, ribosomal binding site, and terminators. In eukaryotes generally control sequences include promoters, terminators and, in some instances, enhancers, transactivators or transcription factors. The term "control sequence" is intended to include, at a minimum, all components the presence of which are necessary for expression, and may also include additional advantageous components.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In case the control sequence is a promoter, it is obvious for a skilled person that double-stranded nucleic acid is used.

The terms "protein" and "polypeptide" used in this application are interchangeable. "Polypeptide" refers to a polymer of amino acids (amino acid sequence) and does not refer to a specific length of the molecule unless otherwise specified in the description. Thus peptides and oligopeptides are included within the definition of polypeptide. This term does also refer to or include post-translational modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring. "Fragment of a sequence" or "part of a sequence" means a truncated sequence of the original sequence referred to. The truncated sequence (nucleic acid or protein sequence) can vary widely in length; the minimum size being a sequence of sufficient size to provide a sequence with at least a comparable function and/or activity of the original sequence referred to, while the maximum size is not critical. In some applications, the maximum size usually is not substantially greater than that required to provide the desired activity and/or function (s) of the original sequence.

The term "antibody" includes, without limitation, chimeric antibodies, altered antibodies, univalent antibodies, bi-specific antibodies, Fab proteins or single-domain antibodies. In many cases, the binding phenomena of antibodies to antigens is equivalent to other ligand/anti-ligand binding. The antibody can be a monoclonal or a polyclonal antibody.

"Sense strand" refers to the strand of a double-stranded DNA molecule that is homologous to a MRNA transcript thereof. The "anti-sense strand" contains an inverted sequence which is complementary to that of the "sense strand".

"Expression" means the production of a protein or nucleotide sequence in the cell itself or in a cell-free system. It includes transcription into an RNA product, post-transcriptional modification and/or translation to a protein product or polypeptide from a DNA encoding that product, as well as possible post-translational modifications.

"Foreign" with regard to a DNA sequence means that such a DNA is not in the same genomic environment in a cell, transformed with such a DNA in accordance with this invention, as is such DNA when it is naturally found in a cell from which such a DNA originates.

In the description of the current invention reference is made to the following sequences of the Sequence Listing and Figures.

SEQ ID NO. 1: amino acid sequence (position 1–298) for syndecan interacting protein (one letter code)

SEQ ID NO. 2: cDNA sequence (position 1–2193) encoding for a polypeptide of 298 amino acids ; ATG start codon at position 149

SEQ ID NO. 3: cDNA sequence together with amino acid sequence encoding syndecan interacting protein

BRIEF DESCRIPTION OF THE DRAWINGS

FIG. 1 (control) and FIG. 2 represent a GFP (green fluorescent protein) staining of CHO cells overexpressing Sycl protein showing a striking change in morphology.

METHODS

Yeast two-hybrid screening

Baits, comprising at least a cytoplasmic domain FYA (corresponds to Phe-Tyr-Ala) as C-terminal sequence of syndecans fused in frame to the DNA-binding domain of Gal4, were constructed by PCR, using the BamHI/SalI restriction sites of the pAS2 vector (Clontech Laboratories), and used to screen a human liver cDNA library (Clontech Laboratories) cloned in pGAD10. The pAS2 plasmids and library were cotransfected in CG1945 yeast cells, and positive clones were selected on triple minus plates (Leu-, Trp-, His-) and assayed for b-galactosidase activity. Positive cDNA clones were cotransfected with all four bait vectors and with the original pAS2 vector cells to confirm the interaction. Mutations in the syndecan and sycl constructs were made by PCR, using the QuickChange site-directed mutagenesis protocol and reagents (Stratagene). All the constructs and mutants that were tested in the matings were confirmed by sequencing.

Cloning of sycl

The insert from the selected clone (3p11) was recloned in pBluescript and completely sequenced. Full length cDNA for sycl was obtained from the sequencing and merging of the I.M.A.G.E. clones #33203 and #285265 (obtained through Research Genetics), identified as containing parts of the sycl sequence (from a BLAST search of the NCBI database of EST Sequences).

Production of GST-fusion proteins

Fusion proteins between glutathione S-transferase (GST) and sycl or parts of sycl, and wild-type or mutant syndecan cytoplasmic domains were produced by cloning the cDNAs into the pGEX-5X-2 vector Pharmacia Biotech) and expression into E. coli BL21 cells. Cells, induced for 3 h with 10 mM IPTG, were suspended in 100 mM NaCl, 1 mM EDTA, 50 mM Tris-HCl, pH 8.0, supplemented with the proteinase inhibitors aprotinine, benzamidine, leupeptine, pepstatin, 6-aminohexanoic acid and PMSF. After treatment with lyzozyme for 1 h, on ice, the fusion protein was recovered from the water soluble phase, and purified by affinity chromatography over glutathione-Sepharose 4B (Pharmacia Biotech).

Surface Plasmon Resonance measurements

300 RU of biotinylated synthetic peptide (32aa), corresponding to the cytoplasmic domain of syndecan-2, were immobilized on the Fc2 surface of a Streptavidin (SA)-sensor chip. Analyte was perfused (10 $\mu$l/min) over the Fc1(control) and Fc2 (capture) surfaces in running buffer (100 mM NaCl, 0.005% surfactant P20, 10 mM HEPES, pH 7.4). Binding was monitored in a Biacore 2000 instrument (Pharmacia Biosensor), and measured as the difference between Fc2 and Fc1 binding curves. The surface was regenerated through three 1 min pulses of 1M NaCl, 0.05 M NaOH.

Production of sycl antibodies

Sycl was tagged with a myc-epitope at its C-terminus and cloned into the pQE-11 prokaryotic expression vector (Qiagen), introducing a 6xHis-tag at the N-terminus of the protein. After expression in E.coli, the 6xHis-sycl-myc protein was extracted in 4M guanidinium cloride and purified by chromatography over a Ni-NTA column (Qiagen), using the myc-tag to monitor the purification of the protein. The protein was used for the immunization of mice and the production of sycl-specific monoclonal antibody, using standard hybridoma technology.

Cell transfections with eGFPsycl

The full length sycl and 3p11 cDNAs were subcloned in pEGFP-C1 using the XhoI restriction sites of the vector.

Additional data relating to the syndecan-interacting protein "syntenin"

1. The second PDZ-domain of syntenin is crucial for the syndecan-syntenin binding interaction:

Prior deletion experiments had indicated that the N-terminal domain of syntenin alone and either of the two PDZ domains of syntenin alone were inactive in binding (the cytoplasmic domain of the) syndecans. Syndecan-binding was limited to the combination of the two PDZ domains (and possibly part of the N-terminal region). Yet, point mutagenesis of K119 (PDZ-1), K203 (PDZ-2), and of the alpha-B helices of PDZ-1 and PDZ-2 in (fall length) syntenin shows that syndecan-syntenin binding involves PDZ-2 (only the mutagenesis of PDZ-2 reduced the binding of GST-syntenin to immobilized syndecan-2 peptide in BIACore experiments). If syndecan binds directly and only to PDZ-2, it remains to be explained why the isolated PDZ-2 domain of syntenin is less active than the paired domains. Together with the failure of (immobilized) syntenin to bind free syndecan-peptide (added in solution) and the evidence that residues 92–298 of syntenin interact with full length syntenin and with the isolated N-termi domain of syntenin, this may indicate that the syndecan-syntenin interaction requires oligomerisation of both syndecan and syntenin.

2. While syndecan binds syntenin via its t-FYA sequence, the specificity of the syndecan-syntenin interaction may involve additional syndecan structural elements:

Syntenin binds to a peptide representing the full length of the syndecan-2 cytoplasmic domain (yeast two-hybrid, GST-fusion protein overlays, and BlAcore experiments) and to a peptide comprising EFYA as its C-terminus. In combination with the mutagenesis experiments (deletions and point mutations of the syndecan-2 peptide sequence) this shows that syndecan-syntenin binding involves the C-terminal FXA sequence of the syndecans. Yet, while some PDZ-proteins other than syntenin interact with Gal4-EFYA fusion proteins in the yeast-two-hybrid assay, these do not interact with Gal4-syndecan baits. This demonstrates that the context upstream of the t-FYA sequence needs to be "permissive" and may help determining the specificity of the syndecan-syntenin (peptide-PDZ) interaction. This implies that, in addition to syndecans, several, but not all proteins terminating with t-FXA may be binding partners (and compete with syndecans) for syntenin.

3. The syndecan-syntenin interaction occurs in situ, but may not be "constitutive":

Clear membrane-recruitment of transiently expressed eGFP-syntenin (fusion protein) and colocalization of this eGFP-syntenin with syndecans was observed in cells that overexpress syndecans. To investigate the possible interactions of the natural molecules, mouse monoclonal antibodies were raised against recombinant human syntenin and used for immuno-purification of endogenous syntenin and determining its associations. In Western blots, these antibodies react with GST-syntenin fusion proteins, but not with the isolated GST-moiety of these fusion proteins. In immuno-fluorescence microscopy, these antibodies stain cells that overexpress eGFP-syntenin (colocalization of red anti-mouse and green eGFP-fluorescence) more intensely than non green-fluorescent cells or cells that express eGFP. This establishes the reactivity of these antibodies with the syntenin peptide. Immunoprecipitation of syntenin from (MDCK) cell extracts with one of these antibodies (mAb 4F6), and development of the immunoprecipitates with anti-syndecan-1 antibody indicates that syndecan-1 co-precipitates with syntenin in subconfluent (spreading, unpolarized) MDCK cells, but not (or clearly less) in confluent (polarized) MDCK cells. This suggests that syntenin-syndecan association occurs in situ, but that it may be conditional upon the state of the cells.

4. Syntenin is a component of the cytoskeleton:

In immuno-fluorescence microscopy of permeabilized (human fibroblasts, CHO, Swiss-3T3, MDCK) cells, two mAbs (4F6 and 4D12, directed against different syntenin epitopes) stain primarily the microtubular network (colocalization with anti-tubulin). Association of (at least a fraction or particular pool of) syntenin with microtubuli is supported by the copurification (and specific enrichment) of the 4F6 epitope with microtubuli during successive cycles of polymerization and depolymerization of microtubuli from pig brain extracts (a classical source and procedure for the isolation of these cytoskeletal structures). A second set of anti-syntenin mAbs (1C8 and 9C10), in contrast, decorates the F-actin-containing stress fibers (colocalization with falloidin-FITC) of (CHO) cells, but not the microtubuli of these cells. An anti-syndecan-1 antibody, finaly, stains primarily the lateral plasma membranes of confluent (MDCK) cells, but reacts primarily with small intracellular vesicles that align with the microtubular network in spreading (MDCK) cells. Whereas none of the transiently expressed eGFP-tagged syntenin constructs (N- or C-terminal tag) colocalized with microtubuli (microfilament association could not be assessed because of some association with microfilaments of eGFP itself), transiently expressed C-terminal myc-tagged M92 syntenin (syntenin lacking the first 91 aminoacids, the N-terminal domain) also aligned with stress fibers, but not with microtubuli (as assessed by anti-myc mAb). Myc-tagged full length syntenin, in contrast, was more cytoplasmic. These data show that syntenin associates with both the actin and the tubulin filament systems of the cells, and that the syntenin-microfilament and syntenin-microtubule associations may involve different parts and conformations of syntenin.

5. Conclusion:

Syntenin links syndecans and syndecan-containing membrane complexes to the cytoskeleton. Syndecans bind to syntenin via their C-terminal ends. These syndecan ends engage the second PDZ domain of syntenin. Theoretically, this leaves the first PDZ domain of syntenin available for the C-terminal peptide from a second syntenin binder, probably a non-syndecan molecule present in the membranes or cytoplasm of the cells, and leaves the N-terminal domain of syntenin available for yet additional binding partners. The documented self-interaction of the paired PDZ domains of syntenin, and their interaction with the N-terminal domain of syntenin suggest that the molecular associations of syntenin are determined by complex intra- and inter-molecular interactions. Syntenin, possibly different pools or conformations of syntenin, directly or indirectly associates with both microfilaments and microtubuli. This demonstrates that gyntenin functions as an adaptor molecule that links syndecans (and possibly other molecules) to the cytoskeleton, e.g. during membrane internalisation (actin filament-associated syntenin) and intracellular membrane traffic (microtubule-associated syntenin).

6. Appendix:

Other syntenin localisations.

Preliminary results, obtained by immuno-fluorescence microscopy using the anti-syntenin mAbs, suggest that (a fraction of) syntenin may also occur in the nucleus (of human lung fibroblast) cells. This suggests that syntenin may also participate in nuclear processes (e.g. regulation of transcription).

What is claimed is:

1. As isolated syndecan interacting protein characterized in that said syndecan interacting protein
   a) contains a tandem repeat of PDZ-domains reacting with the FYA C-terminal amino acid sequence of syndecan,
   b) is represented by a 2.19 kb cDNA encoding a polypeptide of 298 amino acids of SEQ ID NO:1,
   c) contains five tyrosine residues in the amino terminal region represented by amino acids 1–109 of SEQ ID NO: 1, and
   d) said syndecan interacting protein containing no tyrosine residues in amino acids 110–298 of SEQ ID NO: 1.

2. An isolated polypeptide comprising the amino acid sequence according to SEQ ID NO:1 or a functional fragment thereof comprising at least one PDZ domain or the N-terminal region (amino acid positions 1–113 of SEQ ID NO:1), wherein said fragment or N-terminal region binds to syndecan.

3. The polypeptide of claim 2, wherein said functional fragment is located between position 92 and 298 of SEQ ID NO:1.

4. The functional fragment of claim 2, where in said functional fragment is located between positions 113 and 298 of SEQ ID NO:1.

5. A composition comprising a polypeptide comprising the amino acid sequence according to SEQ ID NO:1 or a functional fragment thereof comprising at least one PDZ domain or the N-terminal region (amino acid positions 1–113 of SEQ ID NO:1), wherein said fragment or N-terminal region binds to syndecan.

6. A method for screening compounds that interfere with the interaction between syndecan and syndecan interacting protein, said method comprising:
   a) adding a compound to a solution comprising syndecan and syndecan interacting protein; and
   b) monitoring the interaction between syndecan and syndecan interacting protein.

7. The method according to claim 6, wherein said monitoring comprises a two-hybrid screening assay.

8. The method according to claim 6 wherein said monitoring comprises ligand blot-assays.

9. The method according to claim 6, wherein said monitoring comprises surface plasmon resonance experiment.

* * * * *

UNITED STATES PATENT AND TRADEMARK OFFICE
CERTIFICATE OF CORRECTION

PATENT NO. : 6,368,811 B1
DATED : April 9, 2002
INVENTOR(S) : Jan Grootjans, Pascale Zimmermann and Guido David It is certified that error appears in the above-identified patent and that said Letters Patent is hereby corrected as shown below:

Column 1,
Lines 4-5, change "PRIOR FOREIGN/PCT APPLICATIONS" to -- Art --
Line 7, change "is a continuation of" to -- claims priority from an --
Line 59, after "Their" delete "their"

Column 2,
Line 56, change "Syndecan" to -- syndecan --

Column 6,
Line 3, delete "is meant"

Column 7,
Line 24, change "MRNA" to -- mRNA --

Column 8,
Line 18, change "MRNA" to -- mRNA --
Line 48, change "Sycl" to -- sycl --

Column 10,
Line 12, change "termi" to -- terminal --

Column 18,
Line 36, change "where in" to -- wherein --

Signed and Sealed this

Thirtieth Day of December, 2003

JAMES E. ROGAN
*Director of the United States Patent and Trademark Office*

SEQUENCE LISTING

<160> NUMBER OF SEQ ID NOS: 3

<210> SEQ ID NO 1
<211> LENGTH: 298
<212> TYPE: PRT
<213> ORGANISM: Unknown Organism
<220> FEATURE:
<223> OTHER INFORMATION: Description of Unknown Organism:Syndecan
      Proteins
<220> FEATURE:
<221> NAME/KEY: VARIANT
<222> LOCATION: (119)..(214)
<223> OTHER INFORMATION: Positions 119 and 214 can be K or R

<400> SEQUENCE: 1

Met Ser Leu Tyr Pro Ser Leu Glu Asp Leu Lys Val Asp Lys Val Ile
 1               5                  10                  15

Gln Ala Gln Thr Ala Phe Ser Ala Asn Pro Ala Asn Pro Ala Ile Leu
            20                  25                  30

Ser Glu Ala Ser Ala Pro Ile Pro His Asp Gly Asn Leu Tyr Pro Arg
        35                  40                  45

Leu Tyr Pro Glu Leu Ser Gln Tyr Met Gly Leu Ser Leu Asn Glu Glu
    50                  55                  60

Glu Ile Arg Ala Ser Val Ala Val Val Ser Gly Ala Pro Leu Gln Gly
65                  70                  75                  80

Gln Leu Val Ala Arg Pro Ser Ser Ile Asn Tyr Met Val Ala Pro Val
                85                  90                  95

Thr Gly Asn Asp Val Gly Ile Arg Arg Ala Glu Ile Lys Gln Gly Ile
            100                 105                 110

Arg Glu Val Ile Leu Cys Xaa Asp Gln Asp Gly Lys Ile Gly Leu Arg
        115                 120                 125

Leu Lys Ser Ile Asp Asn Gly Ile Phe Val Gln Leu Val Gln Ala Asn
    130                 135                 140

```
Ser Pro Ala Ser Leu Val Gly Leu Arg Phe Gly Asp Gln Val Leu Gln
145                 150                 155                 160

Ile Asn Gly Glu Asn Cys Ala Gly Trp Ser Ser Asp Lys Ala His Lys
                165                 170                 175

Val Leu Lys Gln Ala Phe Gly Glu Lys Ile Thr Met Thr Ile Arg Asp
            180                 185                 190

Arg Pro Phe Glu Arg Thr Ile Thr Met His Lys Asp Ser Thr Gly His
        195                 200                 205

Val Gly Phe Ile Phe Xaa Asn Gly Lys Ile Thr Ser Ile Val Lys Asp
    210                 215                 220

Ser Ser Ala Ala Arg Asn Gly Leu Leu Thr Glu His Asn Ile Cys Glu
225                 230                 235                 240

Ile Asn Gly Gln Asn Val Ile Gly Leu Lys Asp Ser Gln Ile Ala Asp
                245                 250                 255

Ile Leu Ser Thr Ser Gly Thr Val Val Thr Ile Thr Ile Met Pro Ala
            260                 265                 270

Phe Ile Phe Glu His Ile Ile Lys Arg Met Ala Pro Ser Ile Met Lys
        275                 280                 285

Ser Leu Met Asp His Thr Ile Pro Glu Val
290                 295

<210> SEQ ID NO 2
<211> LENGTH: 2193
<212> TYPE: DNA
<213> ORGANISM: Unknown Organism
<220> FEATURE:
<223> OTHER INFORMATION: Description of Unknown Organism:Syndecan DNA

<400> SEQUENCE: 2
ggcacgaggc gggggcggtg catgacgcgc ctcggggggcg gtcctcgggc g cgcaccgct      60
ctcttacact cggggcctcag aagtccgtgc cagtgaccgg agcggcggcg g cgagcggtt    120
ccttgtgggc tagaagaatc ctgcaaaaat gtctctctat ccatctctcg a agacttgaa    180
ggtagacaaa gtaattcagg ctcaaactgc tttttctgca acccctgcca a tccagcaat    240
tttgtcagaa gcttctgctc ctatccctca cgatggaaat ctctatccca g actgtatcc    300
agagctctct caatacatgg ggctgagttt aaatgaagaa gaaatacgtg c aagtgtggc    360
cgtggtttct ggtgcaccac ttcaggggca gttggtagca agaccttcca g tataaacta    420
tatggtggct cctgtaactg gtaatgatgt tggaattcgt agagcagaaa t taagcaagg    480
gattcgtgaa gtcattttgt gtaaggatca agatggaaaa attggactca g gcttaaatc    540
aatagataat ggtatatttg ttcagctagt ccaggctaat tctccagcct c attggttgg    600
tctgagattt ggggaccaag tacttcagat caatggtgaa aactgtgcag g atggagctc    660
tgataaagcg cacaaggtgc tcaaacaggc ttttggagag aagattacca t gaccattcg    720
tgacaggccc tttgaacgga cgattaccat gcataaggat agcactggac a tgttggttt    780
tatctttaaa aatggaaaaa taacatccat agtgaaagat agctctgcag c cagaaatgg    840
tcttctcacg gaacataaca tctgtgaaat caatggacag aatgtcattg g attgaagga    900
ctctcaaatt gcagacatac tgtcaacatc tgggactgta gttactatta c aatcatgcc    960
tgctttttatc tttgaacata ttattaagcg gatggcacca agcattatga a agcctaat   1020
ggaccacacc attcctgagg tttaaaaattc acggcaccat ggaaatgtag c tgaacgtct   1080
ccagtttcct tctttggcaa cttctgtatt atgcacgtga agccttccg g agccagcga   1140
gcatatgctg catgaggacc tttctatctt acattatggc tggggatctt a ctctttcat   1200
```

-continued

```
ctgatacctt gttcagattt caaaatagtt gtagccttat cctggtttta c agatgtgaa    1260 cttttcaagag atttactgac tttcctagaa tagtttctct actggaaacc t gatgctttt   1320 ataagccatt gtgattagga tgactgttac aggcttagct ttgtgtgaaa a ccagtcacc    1380 tttctcctag gtaatgagta gtgctgtcat attactttag ttctatagca t acttgcatc   1440 tttaacatgc tatcatagta catttagaat gattgccttt gatttttttt t ttaaattct   1500 gtgtgtgtgt gtgtaaaatg ccaattaaga acactggttt cattccatgt a agcattaaa   1560 cagtgtatgt aggtttcaag agattgtgat gattcttaaa ttttaactac c ttcacttaa   1620 tatgcttgaa ctgtcgcctt aactatgtta agcatctaga ctaaaagcca a aatataatt   1680 attgctgcct ttctaaaaac ccaaaatgta gttctctatt aacctgaaat g tacactagc   1740 ccagaacagt ttaatggtac ttactgagct atagcatagc tgcttagttg t ttttgagat   1800 tttttagtca acacataatg gaaacttctt tcttctaaaa gttgccagtg c cactttttaa  1860 gaagtgaatc actatatgtg atgtaaaagt tattacacta aacaggataa a cttttgact   1920 ccccttttgt tcatttgtgg attaagtggt ataatactta attttggcat t tgactctta   1980 agattatgta acctagctac tttgggatgg tcttagaata tttttctgat a acttgttcc   2040 ttttcctgac tcctccttgc aaacaaaatg atagttgaca ctttatcctg a tttttttct   2100 ttttttggt ttatgtctat tctaattaaa tatgtataaa taaagttaca t tttagtctg    2160 tcaaaaaaaa aaaaaaaaaa aaaaaaaaaa aaa                                    2193
```

<210> SEQ ID NO 3
<211> LENGTH: 2193
<212> TYPE: DNA
<213> ORGANISM: Unknown Organism
<220> FEATURE:
<223> OTHER INFORMATION: Description of Unknown Organism:Syndecan DNA

<400> SEQUENCE: 3

```
ggcacgaggc gggggcggtg catgacgcgc ctcggggcg gtcctcgggc g cgcaccgct     60 ctcttacact cgggcctcag aagtccgtgc cagtgaccgg agcggcggcg g cgagcggtt   120 ccttgtgggc tagaagaatc ctgcaaaaat gtctctctat ccatctctcg a agacttgaa   180 ggtagacaaa gtaattcagg ctcaaactgc tttttctgca aaccctgcca a tccagcaat   240 tttgtcagaa gcttctgctc ctatccctca cgatggaaat ctctatccca g actgtatcc   300 agagctctct caatacatgg ggctgagttt aaatgaagaa gaaatacgtg c aagtgtggc   360 cgtggtttct ggtgcaccac ttcaggggca gttggtagca agaccttcca g tataaacta   420 tatggtggct cctgtaactg gtaatgatgt tggaattcgt agagcagaaa t taagcaagg   480 gattcgtgaa gtcatttgt gtaaggatca agatggaaaa attggactca g gcttaaatc    540 aatagataat ggtatatttg ttcagctagt ccaggctaat tctccagcct c attggttgg   600 tctgagattt ggggaccaag tacttcagat caatggtgaa aactgtgcag g atggagctc   660 tgataaagcg cacaaggtgc tcaaacaggc ttttggagag aagattacca t gaccattcg    720 tgacaggccc tttaacgga cgattaccat gcataaggat agcactggac a tgttggttt    780 tatctttaaa aatggaaaaa taacatccat agtgaaagat agctctgcag c cagaaatgg   840 tcttctcacg gaacataaca tctgtgaaat caatggacag aatgtcattg g attgaagga   900 ctctcaaatt gcagacatac tgtcaacatc tgggactgta gttactatta c aatcatgcc   960 tgcttttatc tttgaacata ttattaagcg gatggcacca agcattatga a aagcctaat   1020 ggaccacacc attcctgagg tttaaaattc acggcaccat ggaaatgtag c tgaacgtct   1080
```

-continued

| | | | | | |
|---|---|---|---|---|---|
| ccagtttcct | tctttggcaa | cttctgtatt | atgcacgtga | agccttcccg g | agccagcga 1140 |
| gcatatgctg | catgaggacc | tttctatctt | acattatggc | tggggatctt a | ctctttcat 1200 |
| ctgataccct | gttcagattt | caaaatagtt | gtagccttat | cctggtttta c | agatgtgaa 1260 |
| ctttcaagag | atttactgac | tttcctagaa | tagtttctct | actggaaacc t | gatgctttt 1320 |
| ataagccatt | gtgattagga | tgactgttac | aggcttagct | ttgtgtgaaa a | ccagtcacc 1380 |
| tttctcctag | gtaatgagta | gtgctgtcat | attactttag | ttctatagca t | acttgcatc 1440 |
| tttaacatgc | tatcatagta | catttagaat | gattgccttt | gatttttttt t | ttaaattct 1500 |
| gtgtgtgtgt | gtgtaaaatg | ccaattaaga | acactggttt | cattccatgt a | agcattaaa 1560 |
| cagtgtatgt | aggtttcaag | agattgtgat | gattcttaaa | ttttaactac c | ttcacttaa 1620 |
| tatgcttgaa | ctgtcgcctt | aactatgtta | agcatctaga | ctaaaagcca a | aatataatt 1680 |
| attgctgcct | ttctaaaaac | ccaaaatgta | gttctctatt | aacctgaaat g | tacactagc 1740 |
| ccagaacagt | ttaatggtac | ttactgagct | atagcatagc | tgcttagttg t | ttttgagat 1800 |
| tttttagtca | acacataatg | gaaacttctt | tcttctaaaa | gttgccagtg c | cacttttaa 1860 |
| gaagtgaatc | actatatgtg | atgtaaaagt | tattacacta | aacaggataa a | cttttgact 1920 |
| cccctttgt | tcatttgtgg | attaagtggt | ataatactta | attttggcat t | tgactctta 1980 |
| agattatgta | acctagctac | tttgggatgg | tcttagaata | tttttctgat a | acttgttcc 2040 |
| ttttcctgac | tcctccttgc | aaacaaaatg | atagttgaca | ctttatcctg a | ttttttttct 2100 |
| ttttttttggt | ttatgtctat | tctaattaaa | tatgtataaa | taaagttaca t | tttagtctg 2160 |
| tcaaaaaaaa | aaaaaaaaaa | aaaaaaaaaa | aaa | | 2193 |